United States Patent

Pormale et al.

[11] 4,005,070
[45] Jan. 25, 1977

[54] POLYMER DERIVATIVE OF -DIETHYLAMINOETHYL ESTER OF P-AMINOBENZOIC ACID WITH CELLULOSEGLYCOLIC ACID, METHOD OF PRODUCING AND APPLICATION THEREOF

[76] Inventors: Milda Jaovna Pormale, ulitsa Suvorova, 104, kv. 10; Nadezhda Alexandrovna Kashkina, ulitsa Talsu, 9/11, kv. 22; Arvid Janovich Kalninsh, ulitsa Sverdlova, 8, kv. 3; Varvara Nikolaevna Sergeeva, bulvar Rainisa, 11, kv. 2; Janis Alexandrovich Surna, ulitsa M.Kaiju, 3, kv. 3; Janis Shusters, ulitsa Kvcles, 15, korpus 4, kv. 30; Modris Jaowich Melzobs, ulitsa Veidenbauma, 1/3, kv. 3a; Waldis Danielowich Mikazhan, ulitsa Marupes, 17, kv. 32; Indulis Waldowich Purwinsh, ulitsa Marupes, 17, kv. 35; Antons Petrowich Skutelis, ulitsa Marupes, 17, kv. 32; Martinsh Aleksandrowich Liepinsh, ulitsa dzirtsiema, 91, kv. 40, all of Riga, U.S.S.R.

[22] Filed: Nov. 30, 1971

[21] Appl. No.: 203,470

[52] U.S. Cl. .................... 536/66; 424/78; 424/310; 424/362; 536/58; 536/43; 536/84; 536/76

[51] Int. Cl.$^2$ ............... A61K 31/245; C08B 13/00

[58] Field of Search ......... 260/9, 212, 230 R, 214, 260/229; 424/78, 310

[56] References Cited
UNITED STATES PATENTS

| | | | |
|---|---|---|---|
| 2,518,525 | 8/1950 | Curtis | 424/310 |
| 2,703,777 | 3/1955 | Feinstein | 424/361 |
| 3,812,099 | 5/1974 | Kashkina | 260/213 |
| 3,903,269 | 9/1975 | Kashkina et al. | 424/180 |
| 3,928,562 | 12/1975 | Pormale et al. | 424/78 |

Primary Examiner—Edward Woodberry
Attorney, Agent, or Firm—Holman & Stern

[57] ABSTRACT

A novel substance, viz., the salt of β-diethylaminoethyl p-aminobenzoate with celluloseglycolic acid has the following general formula:

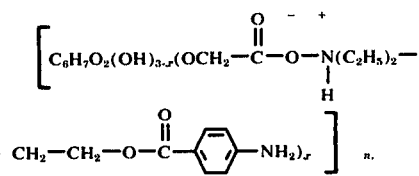

where
 x stands for the degree of substitution ranging from 75 to 100
 n stands for the degree of polymerization ranging from 30 to 120.

A method of producing said compound comprises reacting β-diethylaminoethyl p-aminobenzoate with celluloseglycolic acid in an aqueous medium, whereupon the final product is isolated.

The aforementioned compound, viz., the salt of β-diethylaminoethyl p-aminobenzoate with celluloseglycolic acid is the active principle of a local anesthetic drug. The proposed drug finds application in medical practive as an anesthetic in infiltration, conduction or spinal anesthesia, as well as in surface anesthesia.

4 Claims, No Drawings

POLYMER DERIVATIVE OF -DIETHYLAMINOETHYL ESTER OF P-AMINOBENZOIC ACID WITH CELLULOSEGLYCOLIC ACID, METHOD OF PRODUCING AND APPLICATION THEREOF

The present invention is concerned with a novel substance, viz., the salt of β-diethylaminoethyl p-aminobenzoate, as well as with a method of its production and application.

The novel substance, according to the invention has the following general formula:

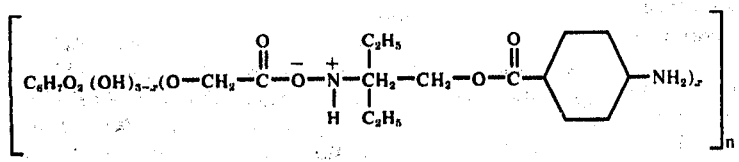

where:
$x$ stands for the degree of substitution ranging from 75 to 100;
$n$ stands for the degree of polymerization ranging from 30 to 120.

Said compound is essentially an amorphous substance, slightly yellowish colour, hydroscopic, readily soluble in water, insoluble in organic solvents, decomposable under the effect of alkali.

Said the salt of βdiethylaminoethyl p-aminobenzoate with celluloseglycolic acid possesses biological activity and, according to the invention is the active principle of a local anesthetic remedy.

In the mechanism of its action said preparation does not differ from procaine and belongs to the group of esters of n-aminobenzoic acid. The preparation in question possesses higher activity and longer duration of its action as compared to procaine. A comparison test of the local-anesthetic effect of the herein-proposed compound and that of procaine was conducted by the method of Bulbring and Wajda in guinea pigs by a subcutaneous injection of the preparation at a dose of 0.25 ml and 4–7 various concentrations of its solution ranging from 0.06 to 3.66 mmole/l. Anesthetic effect was assumed complete if no skin twitching occurred in response to all the six touches by the injection needle (6 units), whereas a complete restoration of the skin sensitivity was assumed to occur when in two consecutive tests carried out at a 5-min interval, skin twitching was observed after all the six touches (0 units). Time lapse from the moment of a subcutaneous injection of the preparation till a complete restoration of skin sensitivity was adopted as characteristic of the duration of anesthetic effect thereof.

The results obtained have shown the deposition effect of the preparation to increase with an increase of the concentration thereof. Thus, when procaine is injected at a concentration of 3.66 mmole/l the activity of infiltration anesthesia begins to decrease as early as the second half-an-hour of the testing procedure, whereas the at the same equimolar concentration of the herein-proposed preparation does not show a decrease in the activity of infiltration anesthesia until as late as the sixth half-an-hour of the test.

For better comparison of the activity by the Miller and Tainter method there were determined average concentrations ($EC_{50}$) of the substances under study that give a 50-per cent anesthetic effect within the initial 30-min period after injection, as well as a relative activity with respect to procaine. The data obtained show that the herein-proposed preparation has an infiltration anesthetic effect 3.1 times that of procaine, while the duration of said effect due to the preparation proposed herein is 2–3 times as long as that caused by the corresponding equimolar solutions of procaine.

Terminal (surface) anesthesia was compared by the Rénier method in rabbits into whose conjunctival sac there were instilled 2 drops of the solution of the herein-proposed preparation taken at 4–6 different concentrations ranging from 18 to 732 mmole/l. Similar tests were conducted with procaine. Then from the obtained values of Rénier indices an average index was determined within its confidence limits for each of the tested concentrations at P = 0.05. In addition the duration of anesthesia of the cornea was measured by continuing to determine the values of the Rénier index every 5 minutes till a complete restoration of the sensitivity of the cornea occurred, i.e. till the appearing of the nictation reflex in response to the initial touch by a hair.

The power of terminal anesthesia was compared by Vallet's formula. It was found that a 2-percent solution of the drug proposed herein possesses a terminal anesthetic effect 6.6 times, and a 1-percent solution thereof, 4.7 times that of procaine, being at the same time 5–16 times inferior to dicaine as to its surface anesthetic effect. The surface anesthetic effect of the proposed compound was found to be 3–5 times that of an equimolar concentration of procaine. Comparison of equally effective concentrations of the present preparation and dicaine showed that the duration of terminal anesthetic effect of the present preparation on the cornea of rabbits is not inferior to that of dicaine and in some cases is even greater.

Visual observations failed to reveal any substantial difference in manifestations of local irritating effect of the proposed drug as compared with procaine when used for either surface anesthesia or infiltration anesthesia except when extremely high concentrations (about 366 mmole/l) were employed and caused a much less marked irritating effect on tissues than did procaine.

Histological study of various tissues likewise corroborated the absence of irritating effect in the preparation proposed herein. Acute toxicity of the preparation was studied in experiments and 282 white mice of both sexes intraabdominal, subcutaneous and intravenous administration of the preparation thereto. For intraabdominal administration 1-percent solutions were used at a dose of 150–300 mg/kg of animal body weight, whereas for subcutaneous administration 5-percent solutions were used taken at a rate of 400–1000 mg/kg of animal body weight and for intravenous administration, 0.5-percent solutions at a dosage of 30–60 mg/kg of animal body weight. The preparation was administered at each of the abovesaid doses to a group of animals consisting of 6–12 mice. Acute toxicity was determined by the graphic method of Litchfield and Wilcoxon on probit paper by calculating average values within their confidence limits at P = 0.05. It was shown by the results of processing the data obtained that the proposed preparation when administered intraabdominally, was 1.47 times less toxic then procaine and when injected subcutaneously, 1.2 times less toxic than procaine, whereas under intravenous administration the preparation has substantially the same toxicity as procaine.

Acute poisoning by the present preparation has clinically the same external manifestations as those caused by procaine.

The present preparation when used for infiltration and terminal anesthesia is 2.8–4.5 times superior to procaine.

Said preparation was tested on 91 patients to whom would ordinarily have been administered. 38 patients were given local anesthesia by administering a 0.5-percent solution of the proposed preparation, whereupon they were subjected to appendectomy for acute or chronic appendicitis. In all these cases a complete anesthetic effect was attained which lasted as long as 3–8 hours after the operation had been completed, whereas under the same conditions the same concentrations of procaine were far from being at all times causative of complete anesthesia pain in the operating zone reappearing as early as 30–60 min after the operation. In 25 cases from the group of 38 patients there was no need to apply any analgesics from the morphine group, while in the other cases a single injection of morphine (1 ml of a 1-percent solution) or of promedol proved to be sufficient, whereas in the case of procaine anesthesia from 3 to 4 injections were generally required.

14 patients were administered a 0.5–1.0-percent solution of the proposed preparation as a local anesthetic in operations for femoral and inguinal hernias, in subtotal thyroidectomy, segmental resection of the mammary gland, etc. In all these cases good anesthetic effect was attained which lasted 6–12 hours more after the operation which is substantially (3–5 times) superior to the anesthetic effect of procaine taken in the same volume of solutions. In no case whatever did the proposed preparation interfere with the healing of operative wounds nor did it disturb the sterility of the area of the operation.

In 39 patients there were made paranephral, intercostal, intracutaneous, intraosseous and retrosternal anesthetic blocks. In most cases these patients had been subjected previously to procaine blocks which gave but incomplete and transient effect. Application of a 1-percent solution of the proposed preparation resulted in a substantial reduction of pain occuring in all the cases within 24–48 hours. Repeated blocks results in complete relief of pain.

The preparation disclosed herein may be applied in aqueous solutions, as a powder or in the form of films and ointments. According to the invention, distilled water is preferentially used as a solvent or vehicle.

When the preparation is applied for infiltration anesthesia the active principle thereof should preferably be taken in a proportion of 0.45–0.96 wt.%.

When the preparation is used for conduction anesthesia the active principle thereof should preferably be taken in a proportion of 1.8–1.92 wt.%.

When the preparation is employed for intraosseous anesthesia the active principle thereof should preferably be taken in a proportion of 3.6–3.84 wt.%.

When the preparation is utilized for intracutaneous anesthesia the active principle thereof should preferably be taken in a proportion of 0.45–1.92 wt.%.

According to the invention, when applying the proposed preparation in the form of an ointment is it preferable to use aqueous lanolin, vaseline or carboxymethyl-cellulose as an ointment base or excipient. It is likewise preferable that the active principle of the preparation be taken in a proportion of 1.8–3.84 wt.% when preparing an ointment.

The preparation is free from any side effect.

Contraindications for the application of the drug are the same as for procaine.

The object of the present invention is also a method of producing the salt of $\beta$-diethylaminoethyl p-aminobenzoate with celluloseglycolic acid, that is the active principle of the preparation disclosed herein. According to the invention said method consists in that $\beta$diethylaminoethyl ester of P-aminobenzoate acid is made to react with celluloseglycolic acid in an aqueous medium, whereupon the final product is isolated.

It is preferable that the interreaction of $\beta$-diethylaminoethyl p-aminobenzoate with celluloseglycolic acid run at 45°–50° C.

To obtain a high-quality final product $\beta$-diethylaminoethyl p-aminobenzoate and celluloseglycolic acid are preferably used in equimolecular amounts.

The reaction of combination of $\beta$-diethylaminoethyl p-aminobenzoate with celluloseglycolic acid occurs as a polymer-analogous one, i.e., without changing the degree of polymerization of the cellulose-containing charge stock. The reaction proceeds either at room or at an elevated temperature. The termination of the reaction is ascertained by measuring the pH value of the reaction medium which should be between 6.5 to 7.5.

The final product is isolated by precipitating it with acetone or by subjecting the solution to lyophilic drying, its yield being equal to 92–97 wt.%.

For a better understanding of the present invention, the following exemplary embodiments of the method for preparing the compound of the invention are described hereinbelow by way of illustration.

EXAMPLE 1

Celluloseglycolic acid can be prepared as follows: 5 g of cellulose are treated for 1 hour with 100 ml of a 30-percent solution of sodium hydroxide at room temperature, whereupon 15 ml of 30-percent hydrogen peroxide are added thereto. The resultant mixture is allowed to stand at 45°–50° C during 2–3 hours. Then cellulose is dehydrated in a squeezer press to its threefold weight, thoroughly distintegrated and placed in a flask, whereupon 70 ml of isopropanol are added thereto. The resulting mixture is stirred for a period of 1 hour, whereupon 6.0 g of monochloroacetic acid are gradually added thereto at 50°–60° C over 15 minutes. The reaction is complete within 4–6 hours.

The fibrous product thus obtained is separated from the liquid and mixed with 70-percent ethanol while adding 30-percent acetic acid to neutralize excess alkali; thereupon, the liquid is decanted once more and the sodium celluloseglycolate is washed with 70-percent ethanol. The thus-obtained sodium celluloseglycolate acid has a degree of substitution equal to 86 and a degree of polymerization equal to 72, its yield being 6.0 g (91 wt.% of the theoretical).

Then 6.0 g of the above-obtained product are dissolved in 100 ml of water and the solution is passed through a cation-exchange resin in the H-form (exchange capacity 4.7 mg-equiv/g).

To 100 ml of a 5-percent solution of the product there are added 4.62 g of β-diethylaminoethyl ester of n-aminobenzoic acid. The reaction proceeds under constant stirring at room temperature for 12 hours, the reaction being stopped when the pH equals 6.9. The resultant solution is filtered and subjected to lyophilic drying to obtain 9.25 g of the final product (96 wt.% of theory).

Calculated, per cent: N, 5.69; β-diethylaminoethyl ester of n-aminobenzoic acid, 48.0;

Found, per cent: N, 5.66; β-diethylaminoethyl ester of n-aminobenzoic acid, 47.9.

EXAMPLE 2

10 g of the sodium celluloseglycolate having a degree of substitution of 0.90 and a degree of polymerization of 500 are mixed with 100 ml of water, whereupon 2 ml of 30-percent hydrogen peroxide are added to the resulting mixture. Then the mixture is kept at 45° C during 2-3 hours, filtered and passed through a cation-exchange resin in the H-form. The thus-obtained celluloseglycolic acid has a polymerization degree equal to 76.

To 100 ml of the thus-obtained 5-percent solution of celluloseglycolic acid are added 4.83 g of β-diethylaminoethyl ester of n-aminobenzoic acid. The process is run at 45° C for 0.5 hour until the pH value of the solution is equal to 6.8. The solution obtained is filtered and dried lyophilically to obtain 9.53 g of the final product (97 wt.% of theory).

Calculated, per cent: N, 5.82; β-diethylaminoethyl ester of n-aminobenzoic acid, 49.1.

Found, per cent: N, 5.74; β-diethylaminoethyl ester of n-aminobenzoic acid, 48.9.

What we claim is:

1. The salt of β-diethylaminoethyl p-aminobenzoate with celluloseglycolic acid having the following general formula:

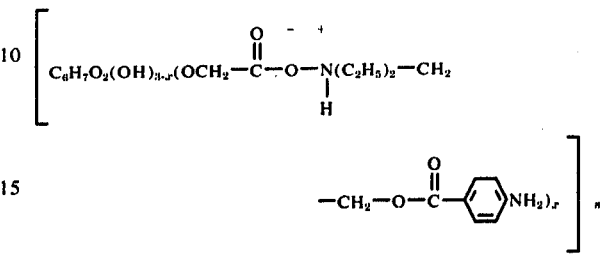

where:
x is the degree of substitution ranging from 75 to 100
n is the degree of polymerization ranging from 30 to 120.

2. A method of producing the salt of β-diethylaminoethyl p-aminobenzoate with celluloseglycolic acid having the following general formula:

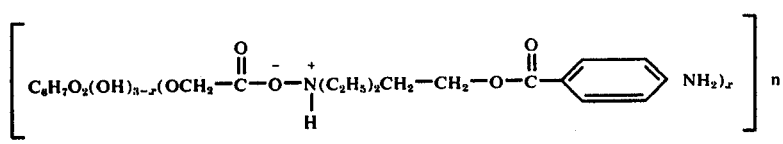

where:
x is the degree of substitution ranging from 75 to 100
n is the degree of polymerication ranging from 30 to 120, said method comprising reacting βdiethylaminoethyl p-aminobenzoate with celluloseglycolic acid in an aqueous medium, terminating the reaction when the pH of the reaction medium reaches from 6.5 to 7.5 and isolating the final product.

3. A method as claimed in claim 2, wherein said reaction is performed at 45°-50° C.

4. A method as claimed in claim 2 wherein said β-diethylaminoethyl p-aminobenzoate and said celluloseglycolic acid are reacted in equimolecular amounts.

* * * * *